US005955123A

United States Patent [19]
Daggy

[11] Patent Number: 5,955,123
[45] Date of Patent: *Sep. 21, 1999

[54] BAKED COMPOSITIONS COMPRISING PSYLLIUM

[75] Inventor: Bruce Paul Daggy, Mason, Ohio

[73] Assignee: The Procter & Gamble Company, Cincinnati, Ohio

[ * ] Notice: This patent issued on a continued prosecution application filed under 37 CFR 1.53(d), and is subject to the twenty year patent term provisions of 35 U.S.C. 154(a)(2).

[21] Appl. No.: 08/734,510

[22] Filed: Oct. 21, 1996

[51] Int. Cl.⁶ .................................................. A21D 8/02
[52] U.S. Cl. ........................... 426/21; 426/615; 426/549; 426/648; 162/150; 514/892; 424/78.01; 424/195.1; 424/442
[58] Field of Search ..................... 426/549, 648, 426/615, 21; 162/150; 514/892; 424/442, 78.01, 195.1

[56] References Cited

U.S. PATENT DOCUMENTS

| | | | |
|---|---|---|---|
| Re. 32,811 | 12/1988 | Rudin | 424/195.1 |
| 906,709 | 12/1908 | Heintz . | |
| 2,278,464 | 4/1942 | Musher . | |
| 3,148,114 | 9/1964 | Fahrenbach et al. | 167/55 |
| 4,089,981 | 5/1978 | Richardson | 426/104 |
| 4,156,021 | 5/1979 | Richardson | 426/104 |
| 4,315,954 | 2/1982 | Kuipers et al. | 426/583 |
| 4,321,263 | 3/1982 | Powell et al. | 424/195 |
| 4,348,379 | 9/1982 | Kowalsky et al. | 424/34 |
| 4,511,561 | 4/1985 | Madaus et al. | 424/195.1 |
| 4,548,806 | 10/1985 | Colliopoulos et al. | 424/35 |
| 4,551,331 | 11/1985 | Rudin | 424/195.1 |
| 4,565,702 | 1/1986 | Morley et al. | 426/93 |
| 4,568,557 | 2/1986 | Becker et al. | 426/618 |
| 4,619,831 | 10/1986 | Sharma | 426/93 |
| 4,668,519 | 5/1987 | Dartey et al. | 426/548 |
| 4,673,578 | 6/1987 | Becker et al. | 426/93 |
| 4,678,672 | 7/1987 | Dartey et al. | 426/19 |
| 4,698,232 | 10/1987 | Shen | 426/572 |
| 4,737,364 | 4/1988 | Kalogris | 424/195.1 |
| 4,747,881 | 5/1988 | Shaw et al. | 106/209 |
| 4,766,004 | 8/1988 | Moskowitz | 426/658 |
| 4,778,676 | 10/1988 | Yang et al. | 424/79 |
| 4,784,861 | 11/1988 | Gori | 426/74 |
| 4,824,672 | 4/1989 | Day et al. | 424/195.1 |
| 4,849,222 | 7/1989 | Broaddus | 424/195.1 |
| 4,871,557 | 10/1989 | Linscott | 426/93 |
| 4,950,140 | 8/1990 | Pflaumer et al. | 424/439 |
| 5,009,916 | 4/1991 | Colliopoulos | 426/615 |
| 5,015,486 | 5/1991 | Franssell et al. | 426/243 |
| 5,143,728 | 9/1992 | Cappel et al. | 424/195 |
| 5,149,541 | 9/1992 | Leis, Jr. et al. | 424/489 |
| 5,219,570 | 6/1993 | Barbera | 424/195.1 |
| 5,384,136 | 1/1995 | Lai et al. | 426/19 |

FOREIGN PATENT DOCUMENTS

| | | | |
|---|---|---|---|
| 0 144 644 | 6/1985 | European Pat. Off. | A23L 1/308 |
| 0 285 201 | 10/1988 | European Pat. Off. | A61K 35/78 |
| 0 387 933 | 9/1990 | European Pat. Off. | A23L 1/308 |
| 2 430 509 | 1/1976 | Germany . | |
| 1 590 507 | 6/1981 | United Kingdom | A23L 1/00 |

*Primary Examiner*—Chhaya D. Sayala
*Attorney, Agent, or Firm*—Betty J. Zea; Mar Cay Hentz; Douglas C. Mohl

[57] ABSTRACT

The subject invention encompasses baked compositions, a therapeutically effective dose of SMOOTH TEXTURE METAMUCIL® and one or more conventional additives used in dough containing compositions. The present invention also encompasses methods for regulating bowel function and/or providing laxation and/or treating hypercholesterolemia and/or increasing fiber consumption in humans or lower animals comprising orally administering the baked compositions according to this invention.

16 Claims, No Drawings

BAKED COMPOSITIONS COMPRISING PSYLLIUM

BACKGROUND OF THE INVENTION

In recent years there has been a growing appreciation of the benefits provided by a high fiber diet. These benefits include the regulation of bowel function, the reduction of gastrointestinal disorders, and reduction of serum cholesterol levels. High fiber intake has also been associated with a decreased incidence of certain types of cancer. The Nutrient Facts Panel for U.S. Food Regulations has determined that the target percentage daily value for dietary fiber is about 25 grams in a 2000 calorie per day diet and about 30 grams in a 2500 calorie per day diet. Unfortunately, the daily diets of a large percentage of the population fall well below these targeted amounts. Therefore, the need exists for uncomplicated and palatable ways for individuals to increase their daily intake of fiber.

One excellent source of fiber is from psyllium husk. Generally, psyllium is introduced into the diet by dispersing it in water or an aqueous beverage which is ingested by the user. Psyllium mucilloid contains natural mucilage and normally forms a gelatinous mass on contact with water. Cookies or other baked compositions have been identified as a useful way to introduce psyllium into the diet. However, attempts to incorporate psyllium into baked goods have historically met with difficulty due to the mucilaginous nature of psyllium. If the psyllium is hydrated before the compositions are baked, an undesirable product results.

A number of methods have been suggested for obviating the problems associated with incorporating psyllium into baked compositions. U.S. Pat No. 5,095,008, Pflaumer et al., issued Mar. 10, 1992 discloses the manipulation of flour, starch and the order of ingredients in addition to "tying up" the water in the cookie dough system prior to mixing in psyllium. U.S. Pat. No. 5,126,150, Piatt et al., issued Jun. 30, 1992, discloses baked cookie compositions where the psyllium is first coated with calcium lactate and optionally a gelatin, prior to mixing. Lai et al., in U.S. Pat. No. 5,384,136, issued Jan. 24, 1995, teaches that psyllium cannot be routinely incorporated into dough products such as bread. Lai et al. further teaches that to overcome the problems with making psyllium-enriched dough products, the psyllium must first be cold extruded to form pellets and then prewetted. Franssell et al., U.S. Pat. No. 5,015,486, issued May 14, 1991, that it is necessary to add a second gum such as guar or bean gum to psyllium to successfully make psyllium-containing microwavable muffins.

By the present invention, it has been surprisingly discovered that psyllium can be added in baked compositions without the many manipulations taught in the prior art. Rather, it has been discovered that psyllium may be incorporated into baked goods simply by adding smooth texture Metamucil® to the other ingredients comprising the dough in the baked compositions. The resulting compositions are palatable, have increased psyllium fiber content, and are easy to make.

It is an object of the present invention to provide methods for regulating bowel function, and/or providing laxation and/or treating hypercholesterolemia and/or increasing fiber consumption by administering baked compositions comprising smooth texture Metamucil® and conventional additives used in dough-containing compositions. It is also an object of the present invention to provide baked compositions having an increased psyllium content which are pleasant tasting and easy to make. These and other objects of the present invention will become readily apparent from the detailed description which follows. All percentages and ratios used herein are by weight unless otherwise specified. Screen mesh sizes used herein are based on U.S. standards. The abbreviation "g", as used herein refers to "grams". The abbreviation "ml" as used herein refers to "milliliters".

SUMMARY OF THE INVENTION

The present invention relates to baked compositions comprising: (a) a therapeutically effective amount of smooth texture Metamucil®; and (b) one or more conventional additives used in dough-containing compositions.

DETAILED DESCRIPTION OF THE INVENTION

The compositions of the present invention are dough-containing compositions comprising smooth texture Metamucil® and one or more conventional additives. Preferred are compositions in the form of cookies, bread, and pancakes. The components of the compositions according to the present invention, and representative amounts, are described in detail as follows. Weight percentages are based on the components prior to baking or cooking. Compositions can also be formulated by varying the level of components in proportion to the levels of components disclosed herein.

Smooth Texture Metamucil®

Psyllium husk, which is from psyllium seeds, is from plants of the Plantago genus. Various species such as *Plantago lanceolate, P. rugelii,* and *P. major* are known. Commercial psyllium husk include the French (black; *Plantago indica*), Spanish (*P. psyllium*) and Indian (blonde; *P. ovata*). Indian (blonde) psyllium husk is preferred for use herein. The psyllium husk is obtained from the seed coat of the psyllium seeds. It is typical to remove the seed coat from the rest of the seed by, for example, slight mechanical pressure, and then to use only the seed coat. The seed coat is preferably removed and sanitized. Sanitization is accomplished preferably by the methods taught in U.S. Pat. No. 4,911,889, issued Mar. 27, 1990 and U.S. Pat. No. 5,229,117 issued Jul. 20, 1993, both to Leland et. al., the disclosures of which are incorporated herein by reference in their entireties.

Metamucil® is an over-the-counter fiber supplement which comprises psyllium husk. Flavored and unflavored versions of Metamucil® are available commercially and are sold by The Procter & Gamble Company; Cincinnati, Ohio. The present inventions comprise smooth texture Metamucil®, (hereinafter referred to as Meta ST). The term "smooth texture Metamucil®", as used herein, refers to any psyllium composition containing reduced particle size psyllium which is agglomerated as described in this document. Reduced particle size husk is disclosed in detail in U.S. Pat. No. 5,149,541, issued Sep. 22, 1992, to Leis, Jr. et al.; and U.S. Pat. No. 5,232,698, issued Aug. 3, 1993, and U.S. Pat. No. 5,234,916, issued Aug. 10, 1993, both to Hord; all of which are incorporated herein by reference in their entireties.

As mentioned above, the psyllium in Meta ST is agglomerated. The agglomerating materials include those selected from the group consisting of water dispersible hydrolyzed starch oligosaccharide, monosaccharide, disaccharide, polyglucose, polymaltose, and mixtures thereof. Preferred are agglomerates and/or coated psyllium, especially psyllium agglomerated with maltodextrin and/or sucrose. The agglomerated psyllium can be agglomerated with and/or contain other materials including edible, water soluble salts such as divalent salts of strong inorganic acids which include magnesium sulfate, calcium sulfate, calcium chloride, zinc sulfate, zinc chloride, and mixtures thereof; and edible acids such as ascorbic acid, phosphoric acid, malic acid, citric acid, and mixtures thereof. Methods for agglomerating psyllium, and materials used with and/or in the agglomeration are described in detail in the following patents, which are incorporated herein by reference in their entireties: U.S. Pat. No. 5,356,618 to Daggy et al., issued Oct. 18, 1994; U.S. Pat. No. 5,340,580 to Barbera, issued Aug. 23, 1994; U.S. Pat. No. 5,234,916, issued Aug. 10, 1993 and U.S. Pat. No. 5,232,698, issued Aug. 3, 1993, both to Hord; U.S. Pat. No. 4,548,806, issued Oct. 22, 1985, and U.S. Pat. No. 4,459,280, issued Jul. 10, 1984, both to Colliopoulos. "Smooth Texture Metamucil®", as used herein refers to the commercial product sold by The Procter & Gamble Company comprising reduced particle size psyllium husk which is agglomerated with maltodextrin, magnesium sulfate and citric acid. Smooth Texture Metamucil®, which is unflavored, is preferred for used in the present compositions. A 5.85 gram amount (approximately 1 rounded teaspoon) of Smooth Texture Metamucil®, unflavored, provides about 3.4 grams of psyllium mucilloid fiber.

The present compositions comprise a therapeutically effective dose of the Meta ST. The term "therapeutically effective amount", as used herein, means an amount of Meta ST which is clinically recognized for regulating bowel function, and/or providing laxation and/or treating hypercholesterolemia and/or which increases the fiber content of the desired baked composition. Such amounts and/or dosing may vary depending on the size and condition of the person ingesting the composition and/or the clinician providing the treatment. However, for increasing fiber intake, a therapeutically effective amount of psyllium mucilloid provided by Meta ST is about from about 2.5 grams to about 20 grams per day. For regulating bowel function and/or providing laxation, a therapeutically effective amount of psyllium mucilloid provided by Meta ST is about from about 2.5 grams to about 30 grams per day; and for reducing hypercholesterolemia, from about 5 grams to about 30 grams per day of psyllium mucilloid provided by Meta ST.

Conventional Additives Used in Dough-containing Compositions

The present invention also comprises one or more conventional additives used in dough-containing compositions. "Dough-containing compositions", as used herein, means any composition containing dough which is produced by conventional baking methods and which is safe for oral administration to humans. Such compositions include but are not limited to: cookies, breads, pancakes, biscuits, muffins, donuts, pizza and pie crusts, breakfast breads such as croissants, bagels, and "English Muffins", pretzels, pastas, and the like. Conventional baking methods include baking by use of a conventional oven, microwave oven, skillet, bread machine, and the like.

The choice of conventional additive(s) and the quantities used in the baked compositions will vary depending on the desired properties of the end product. Therefore, the additives are used in quantities sufficient to achieve desired formulation characteristics according to the formulator's preference. Suitable conventional additives used in dough-containing compositions include: flour components, shortening, sugar or other sweetening agent(s), water, emulsifiers, leavening agents, milk products, egg products, preservatives, antioxidants, and flavoring agents.

The compositions may comprise a shortening component. Shortenings are well-known to those skilled in the art of baking and include solid or plastic, as well as liquid or semifluid, glyceride shortenings derived form animal, and vegetable fats and oils including synthetically prepared shortenings. These glycerides can contain saturated or unsaturated "long-chain" acyl radicals having from about 12 to about 22 carbon atoms such as lauroyl, lauroyleoyl, myristoyl, stearoyl, linolenoyl, arachidonoyl, and the like and are generally obtained from edible oils and fats such as corn oil, cottonseed oils, soybean oil, coconut oil, rapeseed oil, peanut oil, olive oil, palm oil, palm kernel oil, sunflower seed oil, safflower oil, lard, tallow, and the like.

Some preferred shortenings are soybean-based shortenings or oils, hydrogenated soybean-based shortening or oil, corn oil, palm oil, canola oil, hydrogenated palm oil, lard and tallow oils. Of these, "Crisco" brand shortening or oil, which is soybean-based base, is preferred. "Crisco" brand shortening or oil is commercially available and sold by The Procter & Gamble Company, Cincinnati, Ohio. It is preferred that the shortening used in the present invention be in fluid form, i.e., liquid at room temperature or melted, when added to the other ingredients. Low fat shortenings and shortening preparations may also be used. Suitable shortenings can also be formulated with non-absorbable, non-digestible fatty acid esters of polyols. In particular, sucrose polyesters (disclosed in U.S. Pat. No. 4,005,196 to Jandacek et al., issued Jan. 25, 1977, which is incorporated by reference herein in its entirety), and/or other non-nutritive or reduced calorie fat substitute materials are suitable for use in the present compositions. The shortening component comprises from about 0.5% to about 35%, and preferably from about 1% to about 20%, by weight of the dough-containing composition.

One or more flour components may also be included. Any type of flour which is suitable for making dough can be used. Suitable flours include wheat, whole wheat, rye, and corn flours, cottonseed meal and sorghum flour. Wheat flour is preferred for use herein and can be bleached or unbleached. Furthermore, starches may constitute a portion of the flour component of the present compositions. Pregelatinized food starches (e.g., pregelatinized wheat starch, and pregelatinized corn starch) can also be used. Examples of such starches include: Sta-Mist 7415 starch, Sta-Mist 463 starch and Sta-Mist 454 starch (all sold by A. E. Staley Manufacturing Company; Decatur, Ill.). The flour component comprises from about 5% to about 75%, and preferably from about 10% to about 70%, by weight of the dough-containing composition.

Water can also be included in the present compositions. The water content of the dough prior to baking is typically in the range of from about 5% to about 60% by weight of the dough. It is to be noted that the weight percentages of the components herein are by weight of the composition prior to baking. Thus, the dough prior to baking will contain substantially more water than after the dough is baked for a time and at a temperature which is sufficient to reduce the water content in the present compositions.

The present compositions may optionally contain one or more sweetening agents. Suitable sweetening agents include saccharides, disaccharides and polysaccharides such as xylose, ribose, glucose, mannose, galactose, fructose, dextrose, sucrose, maltose, partially hydrolyzed starch or corn syrup solids and sugar alcohols. Sugar components also include materials such as invert sugar syrups, brown sugar, honey, molasses, maple syrups and the like.

Artificial sweetening agents may also be included. Such agents include aspartame, saccharin, cyclamate, acesulfame, gem sweet, L-sugars, trichloro sucrose, aspartyl-D-valine, glycyrrhizin, p-phenetylurea, and neohesperidin hydrochalcone. Preferred artificial sweeteners are saccharin, cyclamate, acesflfame K, and aspartame, sold as Nutrasweet® By G.D. Searle. Sweetening agent can comprise from about 1% to about 40% and preferably from about 30% by weight of the composition.

The present compositions may also comprise one or more emulsifiers. Emulsifiers are frequently referred to as "dough conditioners" because they are used to control the consistency of the dough. Suitable emulsifiers include mono- and diglycerides and fatty aids, sucrose partial fatty acid esters, sorbitan esters of fatty acids, polyoxyethylene sorbitan esters of fatty acids, propylene glycol esters, polyethylene glycol esters, ethoxylated mono- and diglycerides, fumarated ester of monoglycerides or their alkali metal salts, alkanoyl lactylates or their metal salts, lecithins and the like. Preferred emulsifiers include sorbitan monostearate (Span 60), polyoxyethylene sorbitan monostearate (Tween 60), propylene glycol monostearate, glycerol lactopalmitate, sodium stearoyl fumarate, calcium stearoyl-2-lactylate, ethoxylated monoglycerides and lecithin. The present invention can include from about 0.1% to about 30% of an emulsifier, by weight of the composition.

One or more leavening agents may also be included. Non-yeast leavening agents include a source of carbon dioxide such as sodium bicarbonate or potassium bicarbonate, alone or in combination with a leavening acid such as monocalcium phosphate, dicalcium phosphate, sodium acid pyrophosphate, sodium aluminum sulfate, sodium aluminum phosphate, potassium acid tartrate and the like. One or more leavening agents can be included in an amount of from about 0% to about 2%, by weight of the composition.

One or more flavoring agents may also be included. Such agents may be volatile oils, liquids or dry agents which are pharmaceutically acceptable for internal ingestion by humans. Examples of flavoring agents include but are not limited to citrus flavors such as orange and grapefruit; strawberry; cherry; apricot; banana; chocolate; cocoa powder; vanilla and vanilla cream; mint flavors such as peppermint and spearmint; spices such as cinnamon, clove and nutmeg; and nut flavors such as hazelnut, peanut butter and almond. From about 0% to about 30%, by weight of the composition can contain the flavoring agent(s).

The present compositions may also optionally comprise other additives which include milk products such as whole milk, skim milk, buttermilk, whey, concentrated milk product (condensed or evaporated milk), dried milk products, nonfat milk powder, dry whole milk, modified whole milk and the like; egg products including egg whites and egg yolks; other protein sources such as soy protein, preservatives such as sorbic acid, polyhydric alcohols such as glycerol and propylene glycol, emulsifiers such as lecithin, modified celluloses, antioxidants such as ascorbic acid, and coloring agents and dyes.

Optional Components

Dietary fibers other than psyllium may also be included as optional components. Such dietary fibers include: cellulose derivatives (i.e, methylcellulose, hydroxypropylmethyl cellulose, and hydroxypropyl cellulose), and cereal brans such as wheat, corn, barley, rye, oats, rice, and soybean.

Pharmaceutically active agents can also be included. Such agents include laxatives, analgesics, cholesterol reducing agents and are used in quantities to deliver a safe and therapeutically effective amount of the desired pharmaceutically active agent.

Method of Treatment

The present invention also relates to a method for regulating bowel function, and/or providing laxation and/or treating hypercholesterolemia and/or increasing fiber intake, the method comprising the oral administration of a baked composition according to the present invention to a human or lower animal patient in need of such treatment.

Treatment of hypercholesterolemia comprises chronic ingestion in order to lower and maintain a lowered blood cholesterol level. Daily ingestion is preferred, with the ingestion preferably being at two or three spaced intervals throughout the day (e.g. with meals).

The following examples are further describe and demonstrate embodiments within the scope of the present invention. These examples are given solely for the purpose of illustration and are not to be construed as limitations of the present inventions as many variations thereof are possible without departing from the spirit and scope.

EXAMPLE 1

| Components | Amount |
|---|---|
| Enriched White Flour | 480 ml |
| Meta ST[a] | 15 ml |
| Granulated Sugar | 30 ml |
| Wheat Germ | 30 ml |
| Sodium Chloride | 5 ml |
| Canola Oil | 15 ml |
| Water | 240 ml |
| Dry Yeast | 6.25 ml |

[a]Reduced particle size psyllium agglomerated with maltodextrin and citric acid.

Method

Pre-mix dry ingredients and place in a commercially available bread machine. Pour oil and water on the dry ingredients. Place yeast in the dispensing chamber. Initiate "Basic Bread" bake cycle after a 6-hour hold. Slice (about 8 slices in the loaf).

Result

Bread rises to a maximum of approximately 4 centimeters above the loaf pan. The bread has a pleasant, even texture, with no off odors, unmixed section, or other deficiencies attributable to psyllium. The bread loaf provides about 5 grams of psyllium husk fiber.

EXAMPLE 2

| Components | Amount |
|---|---|
| Enriched White Flour | 465 ml |
| Meta ST[a] | 30 ml |
| Granulated Sugar | 30 ml |
| Wheat Germ | 30 ml |
| Sodium Chloride | 5 ml |
| Canola Oil | 15 ml |
| Water | 240 ml |
| Dry Yeast | 6.25 ml |

[a]Reduced particle size psyllium agglomerated with maltodextrin and citric acid.

Method

Pre-mix dry ingredients and place in a commercially available bread machine. Pour oil and water on the dry ingredients. Place yeast in the dispensing chamber. Initiate "Basic Bread" bake cycle after a 2-hour hold. Slice (about 8 slices in the loaf).

Result

Bread rises to a maximum of approximately 4 centimeters above the loaf pan. The bread has a pleasant, even texture, with no off odors, unmixed section, or other deficiencies attributable to psyllium. The bread loaf provides about 10 grams of psyllium husk fiber.

EXAMPLE 3

| Components | Amount |
| --- | --- |
| Enriched White Flour | 465 ml |
| Meta ST[(a)] | 45 ml |
| Granulated Sugar | 30 ml |
| Wheat Germ | 15 ml |
| Sodium Chloride | 5 ml |
| Soybean Oil | 15 ml |
| Water | 240 ml |
| Dry Yeast | 6.25 ml |

[(a)]Reduced particle size psyllium agglomerated with maltodextrin, magnesium sulfate and citric acid.

Method

Pre-mix dry ingredients and place in a commercially available bread machine. Pour oil and water on the dry ingredients. Place yeast in the dispensing chamber. Initiate "Basic Bread" bake cycle after a 2-hour hold. Slice (about 8 slices in the loaf).

Result

Bread rises to a maximum of approximately 4 centimeters above the loaf pan. The bread has a pleasant, even texture, with no off odors, unmixed section, or other deficiencies attributable to psyllium. The bread loaf provides about 15 grams of psyllium husk fiber.

EXAMPLE 4

| Components | Batch A Amount | Batch B Amount |
| --- | --- | --- |
| Pancake Mix | 180 ml | 180 ml |
| Meta ST[(a)] | — | 15 ml |
| 2% White Milk | 120 ml | 120 ml[(b)] |
| Vegetable Oil | 15 ml | 15 ml |
| Egg White | 1 | 1 |

[(a)]Reduced particle size psyllium agglomerated with maltodextrin, magnesium sulfate and citric acid.
[(b)](plus 60 ml, when needed)

Method

Preheat griddle to 190.6° C. Dry mix the pancake mix and Meta ST in Batch B. Add milk, oil, and egg white to both batches. Stir with wooden paddle. If Meta ST batch becomes too thick to pour, stir in additional 60 ml milk. Spoon out about 60 ml onto griddle and cook to desire consistency. Each batch produces about 7 to 8 pancakes.

Results

Batch A pancakes rise to a thickness of approximately 0.5 centimeters. Batch B pancakes rise to a thickness of approximately 1 centimeter. Batch B provides about 5 grams of psyllium husk fiber.

What is claimed is:

1. A baked composition comprising:
   (a) a therapeutically effective dose of psyllium husk wherein the psyllium husk comprises psyllium husk particle sizes distributed such that more than about 90% is smaller than about 45 mesh; and wherein the psyllium husk is agglomerated with an agglomerating material selected from the group consisting of water dispersible hydrolyzed starch oligosaccharide, monosaccharide, disaccharide, polyglucose, polymaltose, and mixtures thereof; and
   (b) one or more conventional additives used in dough-containing compositions; wherein the psyllium is added to the other ingredients comprising the dough in the baked composition.

2. The baked composition of claim 1 wherein psyllium husk comprises particle sizes distributed such that more than about 80% is smaller than about 50 mesh.

3. The baked composition of claim 2 wherein psyllium husk comprises particle sizes distributed as follows: less than about 25% larger than about 60 mesh and at least about 40% smaller than about 80 mesh.

4. The baked composition of claim 3 wherein psyllium husk comprises particle sizes distributed as follows: less than about 10% larger than about 60 mesh, at least about 40% within the range of from about 80 mesh to about 200 mesh, and less than about 50% smaller than about 200 mesh.

5. The baked composition of claim 1 wherein psyllium husk comprises particle sizes distributed as follows: less than about 15% larger than about 80 mesh, at least about 45% within the range of from about 80 mesh to about 200 mesh, and less than about 40% smaller than about 200 mesh.

6. The baked composition of claim 5 wherein psyllium husk comprises particle sizes wherein less than about 5% are larger than about 60 mesh.

7. The baked composition of claim 1 further comprising an edible, water soluble salt selected from the group consisting of magnesium sulfate, calcium sulfate, calcium chloride, zinc sulfate, zinc chloride, and mixture thereof.

8. The baked composition of claim 7 further comprising an edible acid selected from the group consisting of ascorbic acid, phosphoric acid, malic acid, citric acid, and mixtures thereof.

9. The baked composition of claim 7 wherein the psyllium husk is agglomerated with maltodextrin, magnesium sulfate and citric acid.

10. The baked composition of claim 1 wherein the composition is selected from the group consisting of cookies, breads, pancakes, biscuits, muffins, donuts, pizza, pie crusts, breakfast breads, pretzels, and pastas.

11. The baked composition of claim 10 wherein the composition is bread and the conventional additives are a flour component, a shortening component, a leavening agent, and water.

12. The baked composition of claim 10 wherein the composition is pancakes.

13. A method for regulating bowel function in humans or lower animals, the method comprising orally administering to a human or lower animal in need of such treatment a safe and effective amount of the baked composition according to claim 1.

14. A method for treating hypercholesterolemia in humans or lower animals, the method comprising orally administering to a human or lower animal in need of such treatment a safe and effective amount of the baked composition according to claim 1.

15. A method for increasing fiber consumption in humans or lower animals, the method comprising orally administering to a human or lower animal in need of such treatment a safe and effective amount of the baked composition according to claim 1.

16. A method of making the baked composition of claim 1 wherein the psyllium is incorporated into the baked composition by adding the psyllium directly to the conventional additives used in dough-containing compositions.

* * * * *